United States Patent [19]

Watson et al.

[11] Patent Number: 5,418,466
[45] Date of Patent: May 23, 1995

[54] MOISTURE AND SALINITY SENSOR AND METHOD OF USE

[76] Inventors: Keith Watson, 18 Fern Rd., Crafers; Rick Gatto, 93 Coombe Road, Allenby Gardens; Peter Weir, Chino Street, Renmark; Peter Buss, 6 Eucalypt Parade, St Anges, all of South Australia, Australia

[21] Appl. No.: 920,322
[22] PCT Filed: Oct. 11, 1991
[86] PCT No.: PCT/AU91/00467
  § 371 Date: Aug. 21, 1992
  § 102(e) Date: Aug. 21, 1992
[87] PCT Pub. No.: WO92/07251
  PCT Pub. Date: Apr. 30, 1992

[30] Foreign Application Priority Data

Oct. 12, 1990 [AU] Australia ............... PK2767

[51] Int. Cl.$^6$ ............ G01R 27/26; G01V 3/08
[52] U.S. Cl. ............ 324/668; 324/333; 324/439; 331/65
[58] Field of Search ........... 324/333, 663, 668, 332, 324/439; 331/65; 439/150

[56] References Cited

U.S. PATENT DOCUMENTS

| | | | |
|---|---|---|---|
| 1,652,227 | 12/1927 | Zuschlag | 324/333 |
| 2,376,610 | 5/1945 | Millington | 324/333 |
| 2,398,800 | 4/1946 | Millington | 324/333 |
| 2,408,029 | 9/1946 | Buzzoni et al. | 324/333 |
| 2,623,923 | 12/1952 | Zimmerman | 324/333 |
| 2,689,329 | 9/1954 | Zimmerman | 324/333 |
| 2,722,657 | 11/1955 | Janssen | 324/333 |
| 2,920,172 | 1/1960 | Erdman et al. | |
| 4,181,881 | 1/1980 | Preikschat | |
| 4,692,706 | 9/1987 | Mazzagatti et al. | 324/333 |

FOREIGN PATENT DOCUMENTS

| | | | |
|---|---|---|---|
| 282113 | 10/1966 | Australia | 324/333 |
| 0011919 | 5/1979 | European Pat. Off. | |
| 1244309 | 4/1965 | Germany | 324/333 |
| 55-146032 | 11/1980 | Japan | |
| 1088824 | 10/1967 | United Kingdom | 324/333 |
| 0759984 | 8/1980 | U.S.S.R. | 324/668 |
| 1539639 | 1/1990 | U.S.S.R. | |

OTHER PUBLICATIONS

Smith-Rose, R. L. "The Electrical Properties of Soil for Eight Alternating Currents at Radio Frequencies", *Proceedings of the Royal Society of London*, 140,359 (1993) (no month).

Hoekstra, P. and Delaney, A. "Dielectric Properties of Soils at UHF and Microwave Frequencies", *Journal of Geophysical Research*, vol. 79, No. 11 Apr. 24, 1990.

*Primary Examiner*—Marcus Tyz
*Attorney, Agent, or Firm*—Rodman & Rodman

[57] ABSTRACT

The invention relates to a moisture and salinity measurement and in particular to a sensor and its method or use which may provide values for the moisture/complex dielectric constant of a variety of mediums. A sensor apparatus is arranged for indicating the complex dielectric constant and conductivity of a medium and uses a tuned circuit. The tuned circuit oscillates such that the frequency of oscillation is representative of the complex dielectric constant of the medium.

7 Claims, 6 Drawing Sheets

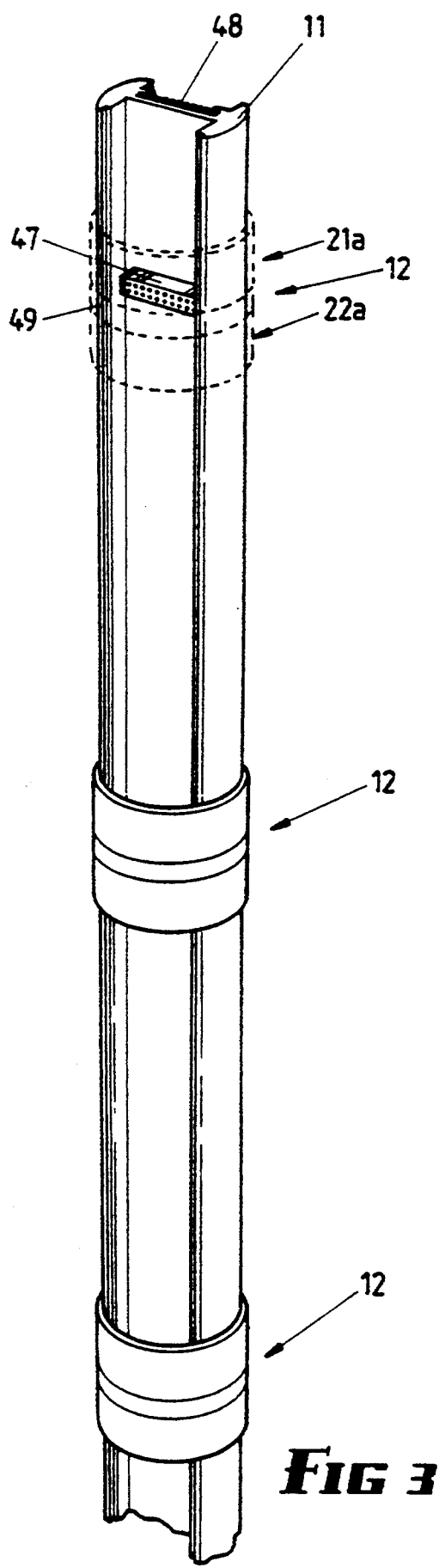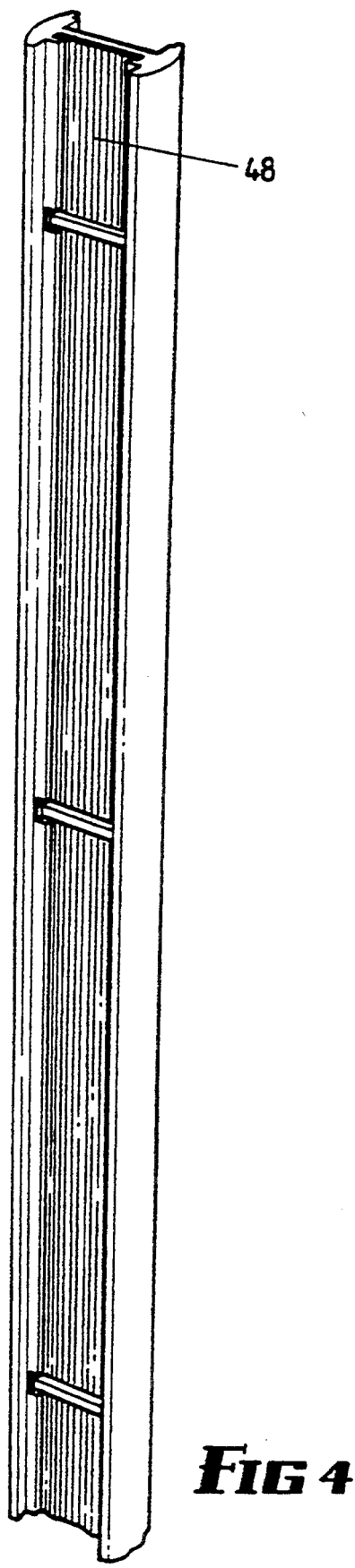

MOISTURE AND SALINITY SENSOR AND METHOD OF USE

This invention relates to moisture and salinity measurement and in particular to a sensor and its method of use which may provide values for the moisture/complex dielectric constant and/or salinity of a variety of mediums in which it is placed, which may include soils, cotton, grain, coal dust and concrete.

BACKGROUND OF THE INVENTION

The invention is primarily directed towards a sensor for determining the moisture/complex dielectric constant and/or salinity of the medium in which the sensor is placed. To assist in the description of the invention we will use the example of one of its many uses, that of measuring the water and salinity content of soil but it will be understood that this is only an example and is not intended to be limiting in any way upon the scope of the invention as later claimed herein.

The efficient use of irrigated water for food production should be a primary objective of irrigators where the basic resources i.e. water, fertilisers, etc., are finite, degradable and/or costly. Efficient irrigation involves applying known amounts of water at frequencies which achieve optimum crop yield and quality, in a way which sustains and protects the resources being used. If irrigations are not correctly scheduled, food quality can be reduced, yields suppressed, perched water tables can rise, the degradation of irrigable land hastened and resources wasted. (The technique used to achieve this is referred to as "irrigation scheduling").

Proper irrigation scheduling requires decisions to be made regarding when to irrigate, how much water to use, and where it should be applied. Throughout the world, the irrigation industry recognises that there is a need for the development of an irrigation scheduling system which is inexpensive, accurate, reliable and repeatable. Gathering relevant information as part of this system is currently a very labour intensive and expensive undertaking, due partly to the instrumentation available and partly to the complexity of the situation.

There are many factors which influence irrigation scheduling techniques and the decision making process, comprising the climatic setting (arid, semi-arid etc.), soil texture, spatial variability, water supply (constraints on availability, cost of pumping, water quality), crop (flowering habit, harvest index, stress sensitivity at each stage of growth), irrigation system (degree of control, level of automation), weather (current, short term expected), economics (profit maximising level of irrigation) and last but not least the level of salinity in the soil water solution. The relationship between these factors can be highly complex, and the development of an integrated expert modelling system for practical irrigation scheduling and crop production has therefore been limited.

Much of the aforesaid problem has been due to the difficulty of collecting accurate and extensive data from the field. The development of a successful irrigation scheduling system based on monitoring will depend on the quantity and quality of the information collected. Some of the information related to the needs of a system is readily available and capable of being collated and understood by the agricultural decision maker without the need for specialised equipment.

This includes inventory information about the soil, water supply quantity and quality, the irrigation system, the physiology of the crop and environmental variables such as climatic details.

Of major significance to the success of an irrigation scheduling system is that part of the system which measures the response of the soil to the applied water and the rate of its depletion by the crop grown. Several devices and procedures have in the past been used to obtain soil moisture/complex dielectric constant measurements from which predictive models have been used to assist the irrigation decision making process. The most commonly used equipment and methods of collecting this type of data from the soil are outlined below.

The simplest but most labour intensive method for directly determining soil water content is the gravimetric sampling method. This methodology is the standard by which all other methods are calibrated. However, its high labour content makes it prohibitively expensive and is thus unsuitable for continuous monitoring of soil water conditions. It is also a destructive sampling technique which makes it impossible to return to the same location to determine the quantitative effects of "irrigation scheduling".

Gypsum blocks are simple and inexpensive devices for collecting moisture data in the field, and found favor in the past for these reasons. However, their main disadvantages lie in the uncertainty of calibration, and the short life expectancy of the block. In use the device is placed in the ground from which it absorbs moisture until equilibrium is reached. Then its resistance is measured from which the water content is inferred. However, this relationship varies between blocks and from soil to soil with time, due to changes in the conductivity of the soil solution in which the device is placed. Since moisture characteristics of the block are known to vary according to soil texture, the resistance/water content relationship derived for the block different soils also varies. However, taking into account the variable response of the block with time invalidates the earlier calibration.

Tensiometers are commonly used to schedule irrigations. They are relatively inexpensive instruments and operate by measuring the force with which water is held in the soil. Their major disadvantage is that the upper limit of measuring water potential is −0.8 bar. A further disadvantage is the need for frequent servicing to remove accumulated gases which are forced out of solution by the vacuum induced in the device during its operation.

Finally, the Bordon gauge versions of the tensiometer, which are the most common in use may have low accuracy and poor repeatability in the field.

The neutron probe is now a widely used instrument for measuring moisture content in the field. The probe generates fast neutrons from an internal radioactive source which are emitted into the soil through a cased hole into which the probe has been lowered during the measurement phase. Some of the emitted neutrons are reflected back after colliding with water molecules in the soil, and read by a detector in the base of the probe. A relationship exists between the number of neutrons detected and the water content of the surrounding medium, and by using a calibration equation, soil water content may be determined.

A serious disadvantage of a neutron probe is the required handling of a radioactive source with its attendant safety measures which not only restrict the general use of the device by the decision makers (farmers) but is also time consuming to operate. This device is further disadvantageous because the interpretation of raw data collected from the device further requires skilled analysis and customized computer assistance even before that data can be used in an "irrigation scheduling" system. The device has further disadvantages since it is not normally able to be left in situ over the periods of time required for data collection purposes for the dual reason of radiation element security and the expense of the device.

None of the abovementioned equipment and soil instrument methods permit frequent and efficient collection of data which is required for real-time assessment of the dynamic changes in water storage and movement in the soil being examined. A major reason for the lack of real-time measurement practices to allow objective scheduling by irrigators, apart from cost and labour, has been the inability of most of the systems available to immediately monitor dynamic soil water movement.

SOIL SALINITY

Of further major concern to irrigators has been the extent and influence of soil salts, accumulated under a range of irrigation practices. Assessing soil salinity is complicated by its spatially variable nature due to the influences of varying management practices, water table depth, soil permeability, evapotranspiration rate, rainfall, salinity of the perched groundwater, and the geohydrological environment.

The measurement of the conductivity of a saturated soil extract is recommended as a general method for appraising soil salinity in relation to plant growth. A saturated soil paste is prepared by stirring a soil sample while distilled water is added until a characteristic end point is reached. A suction filter is then used to obtain a sufficient amount of the extract for making an electrical conductivity measurement.

The special advantage of the saturation-extract method of measuring salinity lies in the fact that the saturation percentage obtained is directly related to the field moisture range. The moisture content of the soil-fluctuates between the lower limit represented by a permanent-wilting percentage and the upper, wet end of the available range, which is approximately two times the wilting percentage. Measurements on soils having a considerable textural range indicate the saturation percentage is approximately equal to four times the 15-atmosphere percentage, which in turn, closely approximates the wilting percentage.

The soluble salt concentration in the saturation extract, therefore, tends to be about one half of the concentration of the soil solution at the upper end of the field-moisture range and about one fourth the concentration that the soil solution would have at the lower dry end of the field moisture range. The salt dilution effect that occurs in fine textured soils, because of their higher moisture retention, is thus automatically taken into account. For this reason, the conductivity of the saturation extract can be used directly for appraising the effect of soil salinity on plant growth.

However with this method repeated measurements at the same spatial position in the soil cannot be obtained because it is a destructive sampling technique. In addition to this problem, repeated measurements of salinity with this method are prohibitively expensive because of the high labour content.

Recently, a number of devices have been made available which seek to overcome the limitations and labour intensiveness of this standard technique.

The four-electrode apparatus is one such device which measures the resistance to electric current flow between one pair of electrodes inserted into the soil while current is passed through the soil via another pair of electrodes. By employing an appropriate geometry constant, which varies with electrode configuration, it is possible to determine the specific electrical conductivity of the soil from the resistance measurement and the soil temperature.

A limitation of this method is that it is often difficult to install the probe in dry or stony soil. A more severe limitation is that soil electrical conductivity is not compensated for with changes in soil moisture content. It is a fact that soil electrical conductivity and hence salinity changes if the amount of soil solution carrying a fixed amount of dissolved salts decreases or increases per unit volume of soil.

A further soil salinity sensor using an electrolytic element involves the element being installed in intimate contact with the soil so that ions in the soil water solution will migrate into or out of the pores of the electrolytic element and thereby keep the solution within the element in chemical equilibrium with the soil solution.

Amongst the numerous problems associated with using this type of sensor is that there is a significant time delay for each measurement of salinity, since ions must diffuse in and out of the pores of the electrolytic element in order to change the conductance reading of the element. A time delay of 3-4 hours is typically required for the element to come to equilibrium with the surrounding medium. Also, the initial use of these sensors is delayed for a period of 4 to 7 days in order to remove the entrapped air from the pores of the electrolytic element. Entrapped air in the pores of the ceramic of the electrolytic instrument restricts the flow of ions and results in higher than normal resistance readings (lower conductivities). A further problem is that this sensor is also easily fouled by oil or other contaminates that could soak into the porous surface. In addition there exists the indeterminate question of at what moisture level the soil water suction becomes the limiting factor in using this method. It is known for example that tensiometers measuring the force at which water is held by the soil particles are of limited value beyond a $-0.8$ bar soil water potential. The water film existing between the ceramic cell of the tensiometer and the soil particles start to break up at this point. It therefore seems very unlikely that the ceramic cell of a salinity sensor would outperform a conventional tensiometer cell in this regard.

The preferred method of soil salinity measurement is the electromagnetic (EM) induction method, which uses the imposition of a primary electromagnetic field within the soil to induce an electric current flow, whereby an induced secondary electromagnetic field is directly proportional to soil electrical conductivity. Using electromagnetic measurements taken in both the horizontal and vertical plane at various depths, the electrical conductivity of the various soil depth increments can be estimated using calculations performed automatically by the equipment.

The main obstacle to the use of this method as a salinity measurement device was that the value of electrical conductivity sensed by the EM unit is the result of the cumulative contribution of the individual soil conductivities of the various strata above a certain depth in the soil. Although it has been claimed that these deficiencies have been substantially overcome, by providing corrections for the orientation of the transmitter coil. Therefore, up until the present invention, the EM method is recommended for use in order to isolate areas of difference or similarity in conjunction with the four-electrode probe which acquires more detailed information within regionally similar salinity areas with respect to the distribution of the soil electrical conductivity in the root zone of the crop, under the furrow, and at distances from drip emitters.

It is an aspect of the invention to overcome or eliminate some of the problems associated with the prior art described above and which is not restricted in its application to soil moisture/complex dielectric constant or salinity measurement and which provides a single sensor device which combines both types of measurement.

BRIEF DESCRIPTION OF THE INVENTION

The present invention relates to an integral moisture/complex dielectric constant and salinity sensor which may be used in a networked array of sensors to provide a system which can record, store and eventually display large quantities of substantially continuous data regarding the soil moisture/complex dielectric constant content and salinity concentrations of the soil water solution at discrete layers of the soil profile being monitored.

In an aspect of the invention a sensor apparatus for indicating the complex dielectric constant and conductivity of a medium comprises a tuned circuit having a variable complex impedance means influenced by the variable complex dielectric constant of said medium, an oscillator means adapted to connect to said tuned circuit so as to oscillate at a frequency dependant on the tuned circuit, such that the frequency of oscillation is representative of the complex dielectric constant of the medium and, in a first mode of operation the oscillator frequency is representative of a first complex dielectric constant of the medium, and in a second mode of operation, the tuned circuit is varied-so that the oscillator frequency is representative of at least one second complex dielectric constant of the medium and the difference between an oscillator frequency of the first mode and an oscillator frequency of the second mode is representative of the conductivity of the medium.

In a further aspect of the invention the sensor apparatus is in an air medium, an in the first mode of operation the oscillator means is adapted to oscillate at a frequency above 27 Mhz and in the second mode of operation, the oscillator means is adapted to oscillate at least one frequency below 27 Mhz.

In yet a further aspect of the invention the tuned circuit further comprises a first part having a fixed complex impedance and a second part having a variable complex impedance where, in said second mode said second part of said tuned circuit is varied to change the frequency at which the oscillator means oscillates.

In a further aspect of the invention said second part of said tuned circuit comprises at least two inductive elements of different values and further comprises switch means adapted to connect one or more of said inductive elements into said tuned circuit when said apparatus is in said second mode.

In an aspect of the invention a method of determining the conductivity of a medium using a sensor apparatus as previously defined comprises the steps of:
(a) determine from said first mode of operation of said apparatus a first complex dielectric constant which is substantially representative of the non-conductive component of said medium,
(b) determine from said second mode of operation of said apparatus a second complex dielectric constant which is representative of the conductive and non-conductive component of said medium,
(c) apply a correction for temperature, and
(d) determine the difference between the temperature corrected complex dielectric constants which is representative of the magnitude of the conductive component of the dielectric constant of the medium and which is proportional to the conductivity of the medium.

It is a further aspect of the invention that the free running oscillation frequency in free air provided by the tuned elements is typically approximately 150 MHz or higher and with a change of the said inductive element the free running frequency of oscillation is 10 MHz.

A preferred embodiment of the invention will now be described, but it will be understood that the invention need not be limited to any one or combination of the following elements or features nor to the particular medium (soil) in which the embodiment is depicted.

BRIEF DESCRIPTION OF THE DRAWINGS

In order that the invention may be more clearly understood, reference will now be made to the accompanying drawings, wherein:

FIG. 3 depicts a front view of a framework to support one or more moisture/complex dielectric constant/salinity sensors;

FIG. 4 depicts a rear view of a framework to support one or more moisture/complex dielectric constant/salinity sensors;

DETAILED DESCRIPTION OF THE INVENTION

Figure 1:
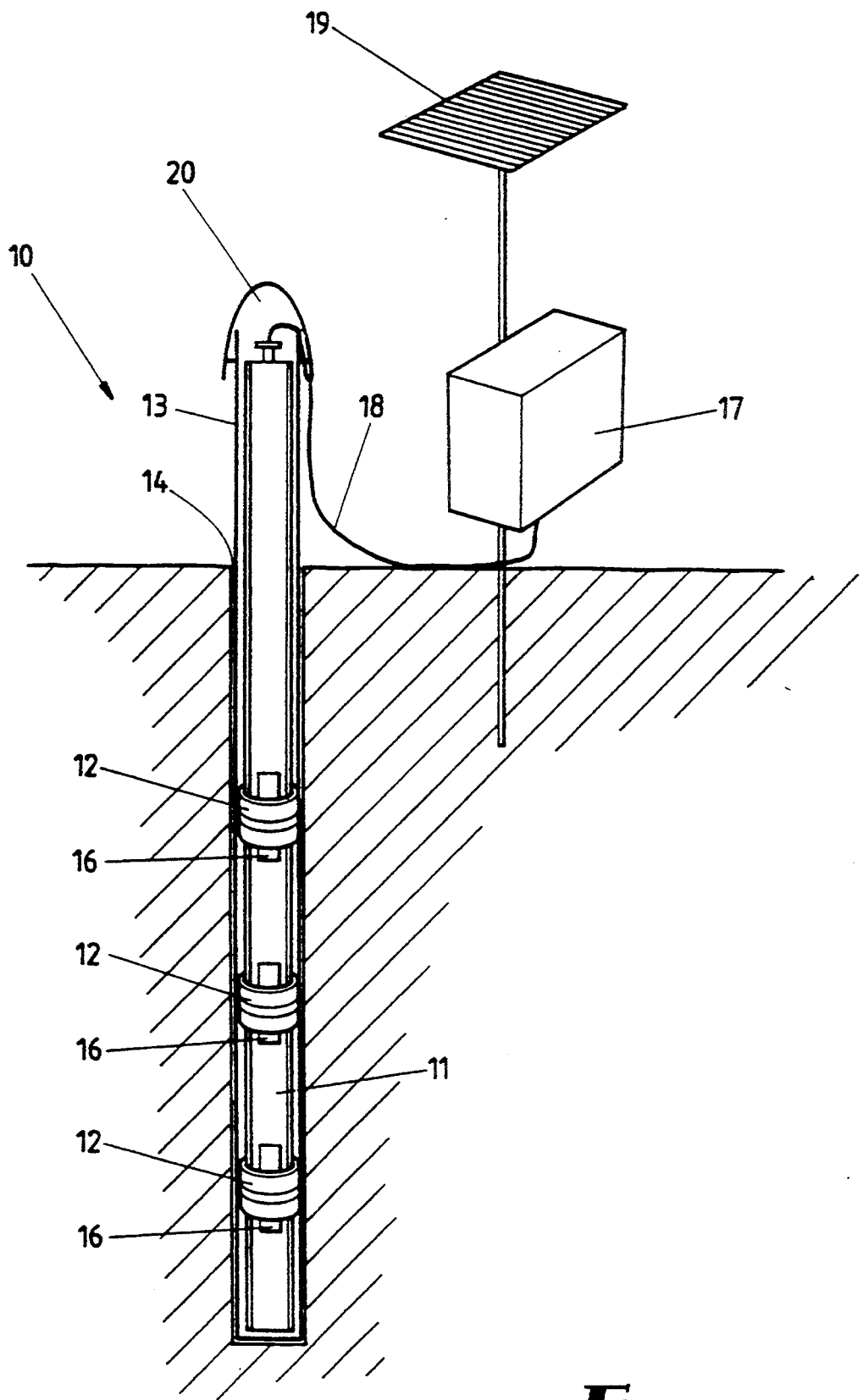
FIG. 1 depicts an embodiment of a soil probe containing three sensors set for operation at three different depths.

This invention describes a sensor capable of determining the moisture/complex dielectric constant content of the surrounding medium, as well as the salinity of the moisture therein.

The embodiment described hereunder will refer exclusively to the use of the sensor in soil and its use in relation to water management decision making. However this should in no way be seen to be limiting as there are many applications to which the sensors can be put as will be apparent to those skilled in the art. Also the sensor of this description may be modified in regard to its physical and electronic configuration and still perform the same function particularly so as to the task of moisture/complex dielectric constant measurement in other media such as grain storage silos, coal repositories and other such environments where accurate and non-contaminating moisture/complex dielectric constant sensors are desirable as well as providing salinity measurement or trend indications where appropriate.

Early work to measure soil moisture using capacitive elements was carried out at low frequencies, in the kHz range, and gave unreliable results with anomalously high values of complex dielectric constant. The importance of interfacial polarization effects in hererogenous materials such as moist soil has been laterally recognised as a distorting characteristic and affected the measurement of soil moisture using capacitive elements at certain frequencies. Thus although the measurements taken reflected the moisture content of the medium they also included numerous other effects. It has been found that the relaxation frequency of the relatively macroscopic electric dipoles associated with interfacial polarization (displacement of charges) occurs at frequencies less than 27 MHz.

Therefore the sensor of this invention in one mode uses frequencies well above 27 MHz when measuring the complex dielectric constant so that such dipole interaction does not contribute to the complex dielectric constant detected By the sensor. Furthermore at these higher frequencies the complex dielectric constant detected by the sensor is primarily a function of soil water content and typically also of particle shape, porosity and the geometrical arrangement of particles.

At a frequency much lower than 27 MHz the complex dielectric constant of soils is approximately inversely proportional to the free running frequency of an oscillator connected into tuned circuit exposed to the soil medium which characteristically levels off at a frequency of about 10 MHz with dielectric values ranging from 5 to 30, depending on the density and moisture content of the soil medium.

As pointed out above, in studying low frequency relaxation, one problem has been the relatively high values of conductivity in soils. The conductivity of saturated soil varies upwardly from 0.3 deci-Siemen per metre (dS/m). Typically the contribution of conductivity to the complex dielectric loss factor at frequencies up to 10 MHz often masks the contribution of relaxation effects. The relation between water content, conductivity, and complex dielectric constant at frequencies below 10 MHz is a strong function of soil type, temperature and the salt concentration in the soil solution.

Thus it is possible to quantify changes over time in the soil conductivity by measuring the complex dielectric constant at high frequencies above 10 MHz and low frequencies below 10 MHz always at a preset known fixed moisture level and at a fixed position in the soil profile. With two parameters being held constant (soil moisture and soil type) changes in the relative complex dielectric constant only can be caused by a variation in two other parameters. These variables are conductance as a function of the dissolved salts in soil water per unit volume and the temperature of the surrounding medium.

The measurement of complex dielectric constant at the low frequency is subject to the interfacial polarization effect, known as the Maxwell-Wagner effect, which leads to an apparent increase in the permittivity of the soil, depending on the conductivity of the soil and its distribution of small colloidal particles.

This has been the cause of confusion and inaccuracy of prior soil water monitoring based on capacitive sensors in the past, because the change in the complex dielectric constant measured by a soil water sensor fixed at a location in the soil profile reflected the interaction of changes in soil water, soil salinity and soil temperature. However high frequency measurements (above 27 MHz) are not subject to the interfacial polarization effects, because the macroscopic dipoles cannot respond to the applied field and hence do not contribute to the complex dielectric constant.

The complex dielectric constant is composed of inductive, capacitive, and conductive components. The conductive component has been shown elsewhere to be frequency dependent. By taking measurements at widely varying frequencies the differences in the complex dielectric constant are an indication of the trend of the conductivity changes of the medium.

Further development of data analysis techniques, in conjunction with corresponding measurement of the temperature of the medium, will provide quantitative values of the conductivity of that medium.

The difference of complex dielectric constant between high and low frequency can be stored within the data processing software as a function of temperature at a known moisture content and correlated with the electrical conductivity of the soil.

To provide an absolute value of volumetric soil water, the sensor output is calibrated at the time of installation against a known volumetric soil measurement of the soil within which the test is conducted. In one example, this calibration can be done using gravimetric analysis.

Typically, the calibration curve is of the form $$Y = a * \mathrm{Exp}\,(b * x)$$

where
Y = volumetric soil water percentage (vsw%)
x = frequency in MHz
a = constant
b = constant It has been found that the soil moisture/complex dielectric constant sensor performs consistently regardless of the soil type thereby further enhancing the utility of the invention since single calibration curve may be used in all soil types and conditions.

Soil conductivity is determined with the same sensor using the second mode of operation as described previously. A number of methods are available to determine the conductivity trends or the absolute conductivity of the medium.

One method of determining the conductivity of a medium using a sensor apparatus of the type described in the embodiment comprises the steps of:

(a) determine from the first mode of operation of the apparatus a first complex dielectric constant which is substantially representative of the non-conductive component of the medium, (b) determine from the second mode of operation of the apparatus a second complex dielectric constant which is representative of the conductive and non-conductive component of the medium, (c) apply a correction for temperature, and (d) determine the difference between the temperature corrected complex dielectric constants, which is representative of the magnitude of the conductive component of the dielectric constant of the medium and which is proportional to the conductivity of the medium.

A method of determining an absolute conductivity of a medium in accordance with the method previously described comprises the further steps of:

(e) repeating at least once the steps (a) to (d) over time, (f) storing the magnitudes with their corresponding first complex dielectric constants, and (g) applying a correlation equation to determine a relative complex dielectric constant from the following equation:

$$K^*(w) = k'(w) - ik''(w)$$

(non-conductive component) (conductive component)

where
$K^*(w)$ = relative complex dielectric constant
$k'(w)$ = relative dielectric constant
$k''(w)$ = relative dielectric loss factor
$w$ = angular frequency and from which the conductivity $\sigma$ (dS/m) can be calculated by application of the following equation:

$$\sigma = k''(w) \times E_o(w)$$

where
$E_o = 8.85 \times 10^{-12} F/m$ = dielectric permittivity of Free space

Thus it is apparent that the difference of frequencies generated by the sensor has a direct relationship to the qualitative conductivity of the medium under measurement and comparison of two or more of these sets of measurement provides a quantitative trend indicator of the changes of the conductivity of the soil medium.

The sensor of this invention may be used as part of a measuring network including sensor control circuitry which also reads multiple sensors which can temporarily store and/or transmit real-time sensor data to an appropriate computer facility, data logger or hand held reading device.

Additionally the raw data of the sensor may be processed using integrative models, that produce easily comprehensible trends and graphs which aid the crop manager in making decisions related to management of irrigations and horticultural practices affecting crop production.

The processes of collecting, storing, transmitting, calibrating, processing, and displaying continuous real-time data into critical values, pictures, graphs, trends, thresholds, tables, forecasts and recommendations to obtain an easy to use decision making tool for the purpose of irrigation scheduling are not described in detail in this specification.

FIG. 1 depicts a sensor apparatus 10 in situ, comprising a support frame 11 for accommodating an array of sensors 12 located within an access tube 13 which has an open top end and a closed bottom end. The access tube is lowered into a prepared hole 14 in the soil 15. The internal diameter of the access tube 13 is preferably large enough to place the support frame into the tube so that the sensors are located substantially against the internal wall of the access tube and therefore as close as possible to the surrounding soil.

It has also been found to be preferable that the hole prepared for the access tube is a close fit to the surrounding soil so that the sensors that are placed therein are also as close as possible to the soil to be monitored. The presence of air gaps against the outer wall of the access tube have been found to adversely affect the accuracy and repeatability as well as the absolute value of the measurements taken from the sensors in the vicinity of those gaps.

Any appreciable gap will artificially reduce the density of the soil surrounding the access tube and may fill with water. In the first instance the air gap will distort the sphere of influence of the sensor and reduce the absolute values of moisture and salinity measured and in the second instance water will distort and reduce the sphere of influence and of course will increase the absolute values of moisture/complex dielectric constant and salinity.

Sensors 12 are shown spaced apart along the support frame 11 which for the purpose of this embodiment are respectively at 10, 20 and 30 cms below the surface of the ground. During the course of the monitoring procedure the sensors remain in those positions, however, it is possible for them to be slid along the side walls of the support frame to collect data from different depths and thus enable reuse of the framework.

An electronic circuit 16 is shown adjacent each sensor apparatus and is used to transduce changes in the characteristics of its adjacent sensor as the moisture/complex dielectric constant and salinity in the surrounding soil 15 changes.

Preferably the respective electronic circuit is located adjacent its sensor upon the support frame 11 so that spurious signals are not picked up on the interconnecting cables between the sensor and the circuit. Each electronic circuit is also adapted to provide a signal representative of the moisture/complex dielectric constant and salinity of the surrounding soil which is then communicated to a data collection device 17 via multistranded cable 18. Preferably, the location of the data collection device 17 is adjacent to the in situ sensor apparatus so that the effect of signal loss and spurious signal interference is minimised on the cable 18.

Power for the sensor apparatus and the data collection device 17 is provided from batteries (not shown) located adjacent the data logger which are in turn charged by the solar-electric convertor (solar panels) 19.

A cap 20 is located over the upper opening of the access tube 13 to prevent the ingress of rain, dirt and insects and thus protect the sensor apparatus from environmental damage.

Figure 2:
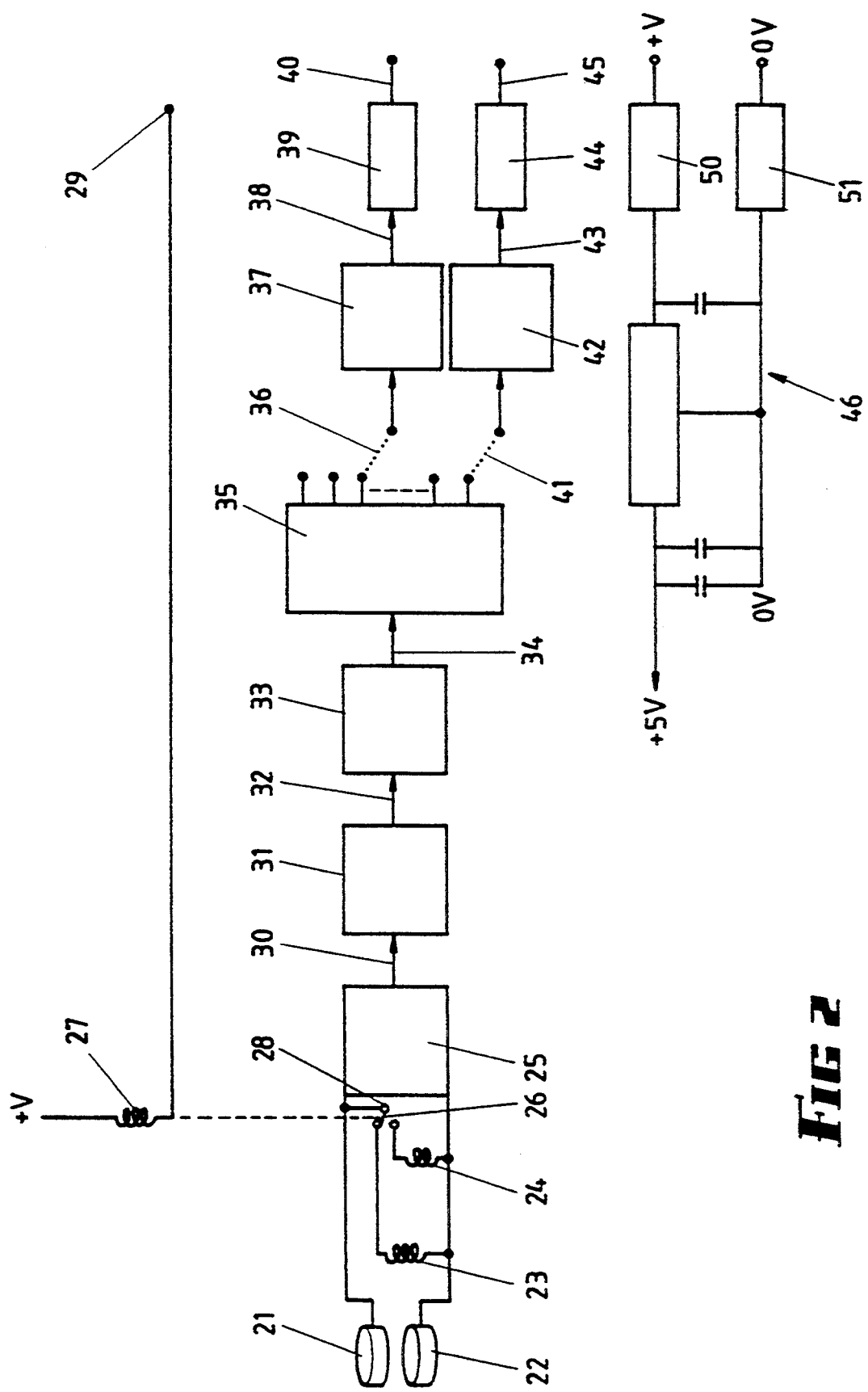
FIG. 2 depicts a circuit embodiment of a soil moisture/complex dielectric constant and salinity measurement sensor.

FIG. 2 depicts a functional block diagram of the soil moisture/complex dielectric constant/salinity sensor apparatus and its associated electronic sensor characteristic detection and transmission circuits. Capacitive (21, 22) and inductive (23, 24) elements in various combinations form a L-C tuning network for oscillator circuit 25.

In this embodiment the primary sensor means comprises a capacitive element in the form of upper 21 and lower 22 conductive rings which, in use, are disposed in spaced relationship to each other to maintain a constant air gap and located in the soil (or other medium to be measured) in a manner depicted in FIG. 1. Alternatively, the inductive and capacitive elements could be reversed.

In combination with one or more inductive elements the oscillator circuit changes its resonant frequency in response to the changing complex dielectric constant of the medium surrounding the capacitive elements. The resonance will change while moisture permeates and moves through the sphere of influence of the capacitive element of the sensor as well as when the salinity of the surrounding medium changes.

In this embodiment one or the other of first 23 and second 24 inductive elements are used in combination with the capacitive element to create a first mode of oscillation which typically has a frequency in the vicinity of 150 MHz for the sensor placed in an air medium.

Thus with the relay contact 26 in the position depicted in FIG. 2 inductor 23 is placed into the oscillator circuit to provide an air medium resonance of 150 MHz. When relay contact 26 is located so as to connect inductor 24 into the oscillator circuit an air medium resonance of 10 MHz is provided in this a second mode.

The relay contact 26 is actuated by the energization of relay coil 27, however, it is possible for the relay contact and relay coil combination to comprise semiconductor, mechanical or other forms of signal relay contacting devices but which perform the functional equivalent of connecting inductors 23 and 24 in and out of the tuned circuit in the oscillator circuit.

The relay contact 26 of this embodiment has a mechanical equilibrium which places the pole terminal 28 in contact with inductor 23 the described first mode of operation. When relay coil 27 is energized via control line 29 going to ground, the relay contact 26 places the pole terminal 28 in contact with inductor 24 to enter the described second mode of operation.

Control of line 29 is located, in this embodiment, remote from the sensor circuit, ideally the control emanates from the data logger and as will be described in detail later in the specification, control is effected when certain conditions are present. Typically though, the relay contact is actuated immediately after an initial complex dielectric constant measurement has been recorded and is then maintained in its second mode position until a second complex dielectric constant measurement has been recorded.

In both the first and second modes the oscillator output 30 which is typically 150/10 MHz for the sensor in an air medium, and is shown being applied to a frequency divider 31 which divides by 100 to provide a first divider output 32 typically 1.5/0.10 MHz.

Output 32 is applied to a signal level convertor 33 which converts the analog output of the divider into a digital pulse train having TTL voltage levels, but which maintains the frequencies of the signal received from the divider.

The digital output 34 is applied to a multi-stage divider 35 which has a plurality of digital output signals which are created by digitally dividing the digital output signal 34. The 12 frequencies provided vary within the range 366 Hz to 750 kHz in a first mode and in a second mode within the range 24 Hz to 50 kHz and of course may be otherwise dependent on the settings used to program or control the operation of the multi-stage divider.

Dependent on the data collection device used, one of the frequency outputs within the range is used to communicate the frequency fluctuations associated with the varying moisture/complex dielectric constant or salinity conditions in the vicinity of the sensor.

Typically, a separate output is used to communicate each of the modes, however, with careful choice of the output frequency of the multi-stage divider both modes could be communicated to the data collection device on one output and time division multiplexing and demultiplexing techniques used to separate out the two types of information or alternatively additional relay contact means could be used to connect the outputs as required to distinguish the two mode signals.

In this embodiment, two of the output frequencies are used, one for the first mode signals and another for the second mode signals. A hardwired connection 36 is provided from a multi-stage divider output to a first driver device 37 of the open collector type, the output 38 of which is applied to a noise suppression device 39 of the low pass filter type for transmission via output 40. A further hardwired connection 41 is provided from another multi-stage divider output to a second driver device 42 of the open collector type, the output 43 of which is applied to a noise suppression device. 44 of the low pass filter type for transmission via output 45.

Outputs 40 and 45 are then capable of being relayed along with the outputs of other sensors via known means to a data collection device 17 as previously described. These means may comprise twisted pair; multi-core cable, coaxial cable, optical fibre or other transmission medium, however in this embodiment multi core ribbon cable is used.

With regard to the driver devices 37 and 42, these may alternatively provide conversion of the digital output signal from the multi-stage divider into a 4–20 mA current loop signal, 0–5 volt signal, infrared or laser modulation of a carrier or radio frequency modulated signal for transmission along an appropriate medium.

A typical regulated power supply circuit is shown at 46 of well known configuration which is used to supply +5 V voltage to the above described circuit elements and includes noise suppression circuits 50 and 51.

In the embodiment shown it can be appreciated that the sensor provides a flexibility in the selection of an output frequency suitable for connection to a wide range of logging and monitoring devices. The circuitry has been designed to be insensitive to temperature drift effects and to provide stable and repeatable frequency excursions.

The sensor has low cost which then makes it economical to use in large numbers thereby increasing the quality and quantity of information available. Indeed the low cost and modular characteristics of the sensor are such that faulty units are merely replaced rather than repaired which is of particular importance in the field as it greatly reduces technical involvement and substantially reduces labour costs.

The sensor of this embodiment operates in the radio frequency band thereby avoiding the use of radioactive sources such as are used in a neutron probe device, or chemical sources as in the mercury tensiometer device both of which are potentially hazardous and dangerous to operators and livestock and/or require a license and special training to operate. It is a further advantage of the sensor of this invention that there is no direct or potentially dangerous indirect contact of the sensor with the medium being tested hence the sensor may be used to measure moisture in soils and food mediums such as grain.

The sensors may operate in a continuous or on request mode. Data may be continuously collected and stored for further processing or it may be sampled from the sensor at predetermined intervals. The reading interval (1 minute ... 10 minutes ... 100 minutes etc.) may vary in accordance with the capacity of the data logging and storage devices or the information may be stored elsewhere continuously or at greater intervals.

FIGS. 3 and 4 depict respectively the front and rear views of a support frame 10 with first upper and lower conductive rings 21a and 22a respectively shown in phantom, in FIG. 3, so that connector 47 is visible. This connector is typical of the type used for access to 20-wire ribbon cable 48 of the type pictorially shown in FIGS. 3 and 4. The sensor electronic circuit 16 is adapted to connect between the conductive rings and the ribbon cable connector 47 and is thereby typically located in the vicinity of the sensors. The upper 21a and lower 22a conductive rings are shown having a spacer 49 between them so as to maintain a constant air gap between them and it is preferable that the sensor is provided as an integral unit so as to reduce the likelihood of separating the rings.

Sensors 12 are shown spaced apart along the support frame 11. The spacing of the sensors is not critical however their absolute depth may be carefully set, thereby providing the flexibility for closely spacing them where required as in complicated soil structures or widely spaced where the soil structure is homogenous. Indeed the spacing need not be regular on any one support frame.

Figure 5:
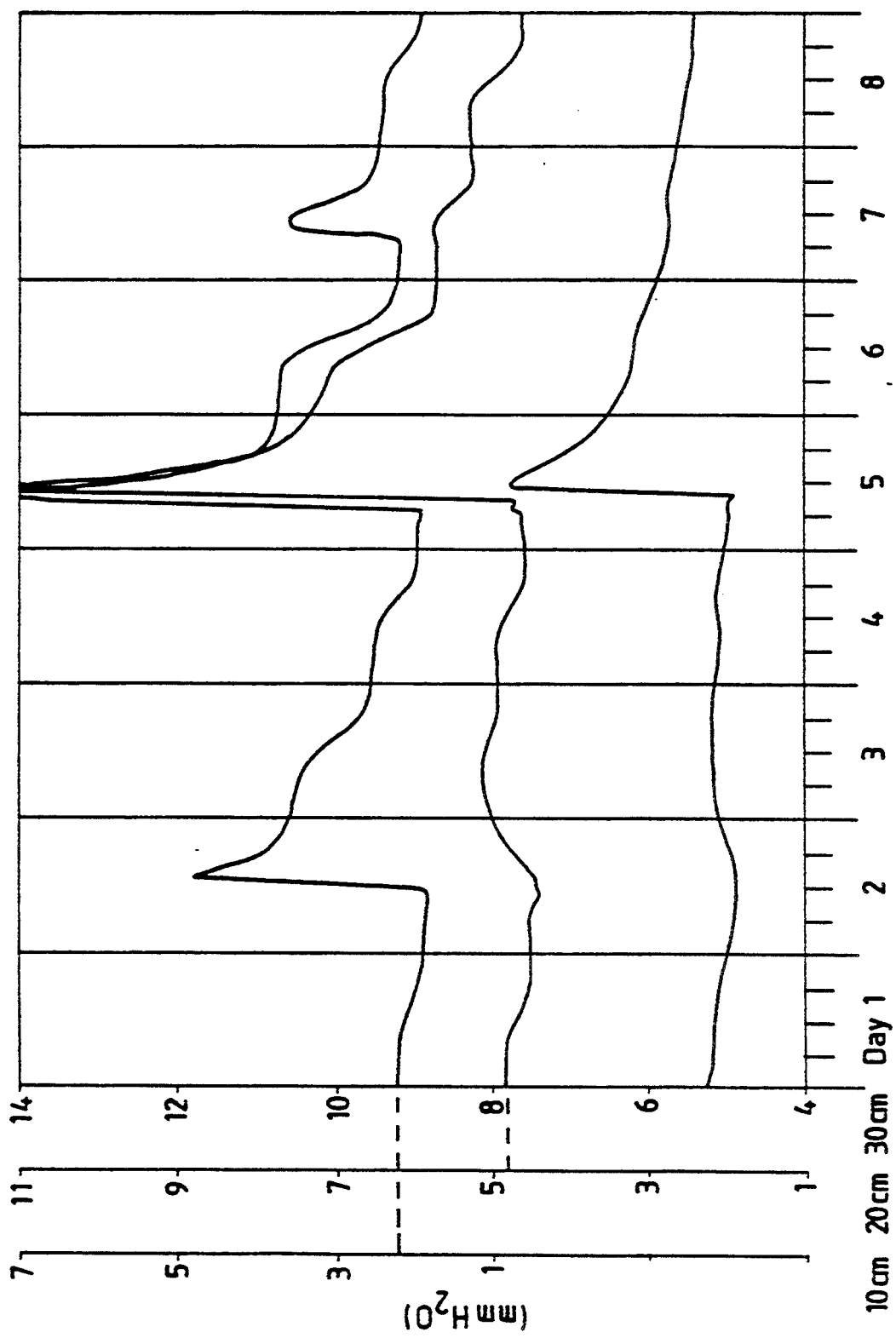
FIG. 5 depicts a graphical representation of the data received from three sensors in operation at three different depths at the same location in a field.

FIG. 5 depicts a graphical representation of the data collected from the soil moisture/complex dielectric constant sensor and its associated electronic circuit in a form particularly suited for interpretation by an irrigation scheduler.

The moisture content measured as total volumetric soil water in mm is shown along the vertical axis for each of three sensors placed at depths of 10, 20 and 30 mm in sandy loam soil harbouring an onion crop against time in days along the horizontal axis.

A two hour irrigation on day 2 is shown to have barely wetted the soil at a 30 cm depth, while the 1½ hour irrigation on day 7 penetrated only to 10 cm. A 4 hour irrigation on the 5th day is clearly seen to have fully penetrated to all the sensors at 10, 20 and 30 cm.

Figure 6:
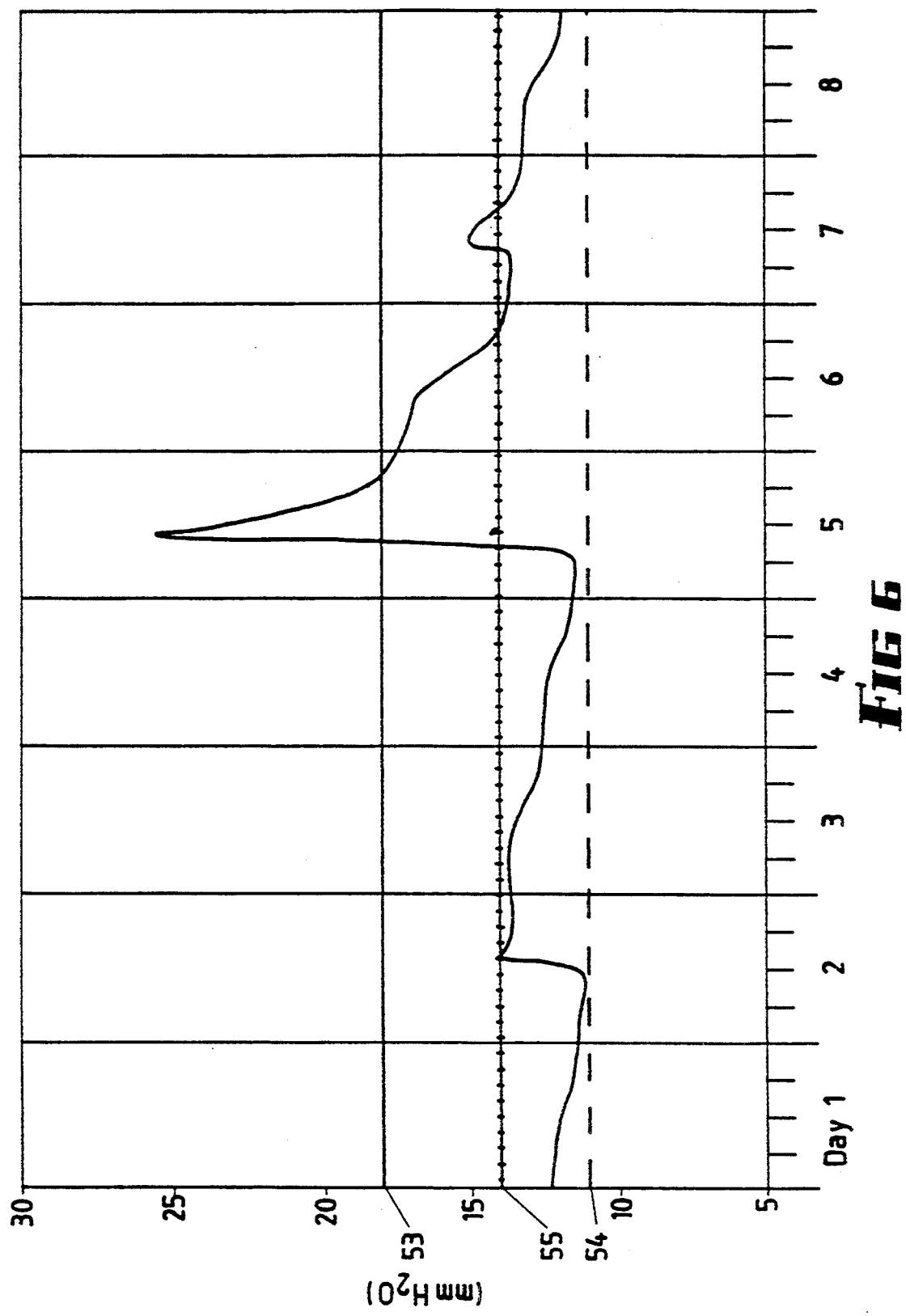
FIG. 6 depicts a combined graphical representation of the data received from three sensors at three different depths at the same location in a field.

FIG. 6 depicts graphically a representation of the combination of the curves of FIG. 5 from which further information regarding irrigation scheduling is obtainable. For example the steep rate of soil water content reduction after the 4 hour irrigation on day 5 is due to the drainage property of the soil, saturation is discernible where the slope of the drainage curve approaches the horizontal as shown by line 53.

The onset of crop water stress can be seen depicted along line 54 since the slope of the curve is approaching the horizontal while the lower level of the optimum soil water content can be seen to lie along the vicinity of line 55 since the slope of the soil water content approaches the horizontal shortly after an irrigation.

Figure 7:
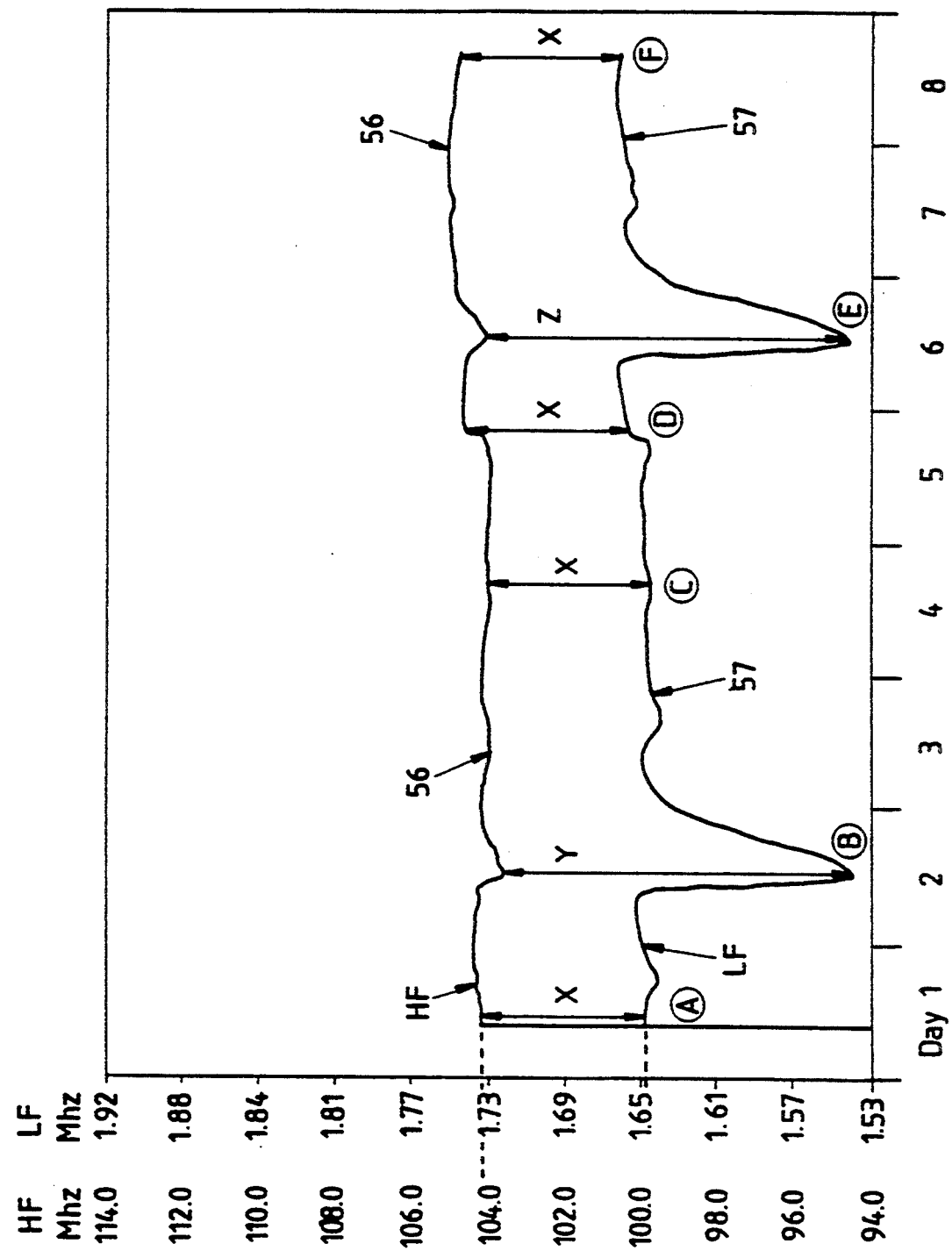
FIG. 7 depicts a salinity measurement response based on controlled application of saline solution to a medium with the sensor in situ.

FIG. 7 depicts graphically a typical representation of the soil salinity variation of the sensor in an idealized measurement condition set up to display the characteristics described previously in respect to the sensor embodiment.

To produce these curves a homogenous sandy loam soil is contained within a test tub into which is placed a sensor at a depth of 30 cms with its associated circuit encased within an access tube in accordance with the embodiment previously described. Water having a salinity concentration of 762 $\mu$S is continuously applied over the soil sample as depicted by the graphs high frequency response during the period day 1 to day 2.

The higher frequency depicts soil moisture while the lower frequency depicts the combined effect of soil moisture and salinity in the test tube.

The high frequency variation is substantially constant as depicted along line 56, while the line 57 depicts an actual saline concentration of about 762 $\mu$S. (A) (curve separation of X).

However, on the 2nd day the saline concentration of the solution was increased to 3560 $\mu$S by adding common salt and the drip flow rate maintained, which is represented on the graph by a lowering of the recorded frequency of the oscillator from 1.65 MHz to 1.53 MHz along line 57 which shows the low frequency mode of operation of the sensor. (B) (curve separation of Y).

Due to the continuous application of a lower saline concentration water, by the 3rd day the slope of the lower frequency mode curve 57 slowly decreases, depicting a leaching effect. This process continues until the 4th day when the low frequency mode curve returns to approximately its initial value. (C) (curve separation of X)

On day 5 a slight reduction of water flow is introduced (D) as reflected in the rise of both curves simultaneously. (curve separation of X)

On the 6th day the saline concentration of the solution was increased to 4180 $\mu$S and is represented by a slightly larger drop of the recorded frequency (E) compared to the drop of frequency caused by the water concentration of the solution introduced on day 2 (see next phase). (curve separation of Z)

As the saline solution dilutes again, by the 7th and 8th days and the flow rate is maintained the slope of the salinity curve 57 slowly decreases, again displaying the leaching effect this continuous flow of water is having. This process continues until the 8th day when salinity measurement returns to the same value as day 1. (F) (curve separation of X). We therefore have indicated that the changes of the lower frequency mode oscillation with respect to changes observed in the high frequency mode are representative of the changes in the soil salinity.

The salinity trends evident in the above test tube environment used however, it is possible for the apparatus to detect a variety of salts which agronomically may indeed in some instances be harmful or beneficial to the crop under study.

Soil salinity is determined with the same sensor using the first and second mode of operation as described previously, storing the signals derived from the measurement of the complex dielectric constant made below and, above 27 Mhz, when the soil temperature measurement is made at the same time typically at reading intervals (1 minute . . . 10 minutes . . . 100 minutes etc.) whereupon they are stored for subsequent processing as sets of high and low frequency measurements.

The sensor output based on measurements made above 27 Mhz predominantly reflect changes of soil moisture/complex dielectric constant content only, whereas measurements made below 27 Mhz reflect changes in the complex dielectric constant due to soil moisture content and/or soil salinity and/or soil temperature as described previously.

Further processing of a collection of measurements allows a comparison of the rate of change of the high and low frequency output. Changes in salinity over time can be analysed by recording the difference or the proportionality of the rate of change derived by the two signals for at least one known soil moisture level over time.

Further processing would scan the data stored to extract all events of a selected soil moisture status (say all the 15% soil moisture events in the past 30 days). These values may be converted to a percentage rate of change and are used to generate a table of the corresponding differences for the corresponding HF (High Frequency) and LF (Low Frequency) measurement for this selected soil moisture event. These values are corrected for temperature.

The table of temperature corrected differences between HF and LF measurements is then calibrated with an equation which converts all temperature corrected differences between HF and LF into electrical conductivity measured in μS or mS/cm. Electrical conductivity values for the selected re-occurring soil moisture event (15% in our example) can now be plotted over time (30 days in our example) indicating the magnitude of increase or decrease of-soil salinity over time.

Finally a crop specific optimum and maximum threshold can be inserted into the graphic display in order to relate salinity monitoring to agronomic management parameters.

We claim:

1. A sensor apparatus for indicating the complex dielectric constant and conductivity of a medium comprising
   oscillator means including a tuned circuit having a complex impedance means wherein a value of the complex impedance means is established by the variable complex dielectric constant of said medium,
   said tuned circuit further comprising a variable impedance means having a first impedance value and a second impedance value for resonating with said complex impedance means respectively at a first frequency and at a second frequency less than said first frequency,
   said oscillator means including means for selecting said first or said second impedance value, a value of said first frequency and a value of said second frequency being dependent on the complex dielectric constant of said medium,
   wherein said selecting means is operative to select said first and said second impedance values sequentially to operate said oscillator means to output said first and said second frequencies sequentially,
   in a first mode of operation of said oscillator means, the first oscillator frequency is representative of a first value of the complex dielectric constant of the medium,
   in a second mode of operation of said oscillator means, the second oscillator frequency is representative of a second value of the complex dielectric constant of the medium, and
   said sensor apparatus further comprises means for obtaining a difference between said first frequency and said second frequency, the difference between an oscillator frequency of the first mode and an oscillator frequency of the second mode being representative of the conductivity of the medium.

2. A sensor apparatus according to claim 1 wherein, in an air medium, said first mode of operation said first frequency is above 27 Mhz and in said second mode of operation, said second frequency is below 27 Mhz.

3. A sensor apparatus according to claim 1 wherein said variable impedance means of said tuned circuit comprises at least two inductive elements of different values and said selector means comprises switch means to connect one said inductive elements into said tuned circuit when said apparatus is in said second mode.

4. A sensor apparatus according to claim 2 further comprising a frame for retaining said oscillator means at a predetermined depth in said medium.

5. A method of determining the conductivity of a medium comprising the steps of:
   (a) placing a sensor apparatus in a medium where said sensor comprises
   an oscillator means comprising a tuned circuit having a variable complex impedance means influenced by the variable complex dielectric constant of said medium where oscillator frequency is representative of the complex dielectric constant of the medium,
   a control circuit connected to said variable complex impedance for controlling said oscillator means into a first mode of operation in which the variable complex impedance means is varied such that the oscillator frequency is representative of a first complex dielectric constant of the medium and also representative of the moisture content of the medium, and further the control circuit controls the oscillator means into a second mode of operation in which the variable complex impedance means is varied such that the oscillator frequency is representative of a second complex dielectric constant of the medium and also representative of the moisture content and conductivity of the medium, wherein the difference between an oscillator frequency of the first mode and an oscillator frequency of the second mode is representative of the conductivity of the medium,
   (b) controlling said control circuit to operate in said first mode and recording on a recording means a representation of said oscillator frequency,
   (c) controlling said control circuit to operate in said second mode and recording on a recording means a representation of said oscillator frequency,
   (d) determining with a computer means according to a calibration equation using the representation of said oscillator frequency from said first mode of operation of said sensor apparatus the moisture content of said medium,
   (e) determining with said computer means according to said calibration equation using the representation of said oscillator frequency from said second mode of operation of said sensor apparatus the absolute combined moisture content and conductivity of said medium as volumetric soil water content,
   (f) determining with said computer means the difference between said first mode and second mode volumetric soil water content, wherein said difference is representative of the conductivity of the medium.

6. A method of determining an absolute conductivity of a medium in accordance with the method of claim 5 comprising the further steps of:
   (g) repeating at least once the steps (a) to (g) over time.

7. A method of determining an absolute conductivity of a medium in accordance with the method of claim 5 comprising the further steps of:
   (h) correcting the difference values for temperature,
   (i) entering each corrected difference value into a calibration equation to provide the absolute conductivity of the medium.

* * * * *